United States Patent [19]
Lee-Kin et al.

[11] Patent Number: 5,717,734
[45] Date of Patent: Feb. 10, 1998

[54] DIGITAL REAL TIME X-RAY SYSTEM INCLUDING MANIPULATOR FOR MICROFOCUS X-RAY

[75] Inventors: Anthony A. Lee-Kin; Richard L. Krantz; William H. Spaulding, all of Phoenix; Stanley W. Trull, Tempe, all of Ariz.

[73] Assignee: AlliedSignal, Inc., Morris Township, N.J.

[21] Appl. No.: 709,546

[22] Filed: Sep. 6, 1996

[51] Int. Cl.⁶ .................................................. H05G 1/02
[52] U.S. Cl. .................................... 378/196; 378/197
[58] Field of Search ............................ 378/176, 177, 378/189, 190, 193, 195, 196, 197, 198, 208, 209

[56] References Cited

U.S. PATENT DOCUMENTS

| | | | |
|---|---|---|---|
| 4,894,855 | 1/1990 | Kresse | 378/196 |
| 5,199,060 | 3/1993 | Kato | 378/176 |
| 5,602,889 | 2/1997 | Oldendorf et al. | 378/195 |

*Primary Examiner*—Don Wong
*Attorney, Agent, or Firm*—James W. McFarland

[57] ABSTRACT

A digital real time x-ray system includes a lead room and a control room. The lead room houses a conventional x-ray source and a microfocus x-ray source and a manipulator for the microfocus x-ray source. The manipulator includes a first bracket which supports the microfocus x-ray source, a second bracket which supports an inspection tray and a third bracket which supports an image intensifier. The first, second and third brackets are controlled for single axis movement and the inspection tray is controlled for two axis movement to allow for accurate positioning of parts being x-rayed.

9 Claims, 6 Drawing Sheets

DIGITAL REAL TIME X-RAY SYSTEM INCLUDING MANIPULATOR FOR MICROFOCUS X-RAY

CROSS REFERENCE TO RELATED APPLICATIONS

This application is related to U.S. application Ser. No. 08/709,547 filed Sep. 6, 1996 by the present inventors entitled Digital Real Time X-Ray System Including Manipulator for Conventional X-Ray (File No. 170-95-047).

BACKGROUND OF THE INVENTION

Modern technology utilizes all types of images as sources of information for interpretation and evaluation. These images can range from portions of the Earth's surface viewed from orbiting satellites to the internal composition of a complex structure seen with the aid of radiographs. The proliferation of these bases of pictorial data has created the need for a vision-based automation that can accurately and rapidly extract the useful information contained in these various images. Many of these requirements are being met through the relatively new technology of digital real time X-ray.

Digital real time X-Ray (DRTX) combines computer applications with modern image sensing to perform various forms of image enhancement, pattern recognition, measurements, increased resolution and distortion correction. The technology of mating both conventional and microfocus x-ray systems with digital real time x-ray technology provides the opportunity to merge older technologies with new/aggressive methods.

Prior to the present invention x-ray testing of both cast and weld components, as used, for example, in the aerospace field, required the use of x-ray film, lengthy developer cycles and numerous component orientations to achieve full coverage of the components being tested.

Real time x-ray systems (RTX) are filmless by design and also provide a continuous opportunity to save inspection costs. The RTX system of the present invention is unique to industry standards, since its operating function has a dual mode capability. That is to say, the system of the present invention utilizes both a microfocus x-ray tube for inspecting nonmetallics and thin-wall metallics and a conventional x-ray tube for inspecting thicker areas.

For purposes of appreciating the present invention, it will be understood that components presently subject to x-ray inspection require weld quality verification or component inspection for small internal discontinuities in ceramic materials. By passing ionizing radiation through a component onto an x-ray film, a latent image is produced after the film developing process. Then the resulting film is viewed/evaluated by certified radiographers per the requirements of the engineering drawings/specifications.

The present invention still uses the same radiation-producing equipment. However, in lieu of x-ray film, an image intensifier is used. An image intensifier is a device that captures the radiation beam, converts the radiation into electrons (in the form of light), amplifies same and outputs the result to a sensitive video camera. In turn, the data on the camera is sent to high-resolution cathode ray tubes (CRT's).

The RTX is then viewed on the CRT. Relevant x-ray indications are interpreted in real time and then copied onto video tape for record retention, as the case may be. When it is necessary to obtain optimum resolution, the RTX image is digitized, using various computer image enhancement subroutines. The ability to manipulate the basic image structure generally provides the required high resolution images, making the radiographer's task somewhat easier by permitting superior interpretations of suspect indications.

By working from the original (analog) image, various subroutines are placed together, starting with the initial digitization. Once an image is digitized, a rapid succession of computer programs extracts pertinent data from the original image by filtering pictorial noise, averaging for clarity and transformations for high resolution.

SUMMARY OF THE INVENTION

This invention contemplates a digital real time x-ray system which significantly reduces the cost of x-ray inspection.

The implementation of the present invention requires two rooms: a lead room and a control room. The lead room is a single lead lined room housing two distinct x-ray sources that share a common system for processing real time x-ray images. This room contains a manipulator which mounts an image intensifier that can be oriented in two positions to be bombarded by the two different x-ray sources: one generating up to 160 kilovolts (kv), 2 miliamps (ma), and the other up to 320 kv, 5 ma.

The x-ray control room is separate from the lead room and contains the x-ray controllers, and all computer and video equipment necessary for processing x-ray images as well as operating various motion control systems.

The 160 kv system uses an x-ray tube with a small diameter focal spot which provides microfocus abilities. This system is ideal for x-ray testing thinner cross sectional parts. An x-ray tube for the purposes intended is manufactured and marketed under the registered trademark Fein Focus.

The 320 kv system uses a Phillips or equivalent x-ray tube with a larger focal spot which is suitable for x-ray testing larger denser materials and thicker components. Both systems can be motion controlled.

The present invention allows the use of two x-ray sources sharing a common room, thus eliminating the cost of constructing two separate lead lined rooms, having two image intensifiers, imaging cameras, surveillance cameras, monitors, motion controlled tables, etc.

The present invention is capable of x-raying a variety of metallic and non-metallic parts such as aluminum, stainless steel, inconel, magnesium and ceramics. In addition, the conventional x-ray method is not eliminated. The use of x-ray film is still available for extremely large and/or thick parts, by simply bypassing the real time features.

It is to be emphasized that the system is coupled to a state-of-the-art computer image enhancement system, using imaging software which provides the ability to acquire analog x-ray video images in a real time mode, convert these video signals to digital format and process the binary data into a resultant composite enhanced image. The output is a binary data file, which when viewed on the computer's output monitor, provides a 3-dimensional image of the x-ray stripped of any noise (x-ray scattering effects). The use of computer image enhancement and motion control provides the ability to reconstruct separate real time x-ray images and form a composite picture representing an image of high clarity and definition. Reduced cycle times and system repeatability is enhanced with the implementation of pre-programmed subroutines. These programs automatically preset all the major manipulator positions, i.e. x-ray tube, intensifier, part being tested, etc. which collectively provide uniform setups and test results.

DETAILED DESCRIPTION OF THE INVENTION

Figure 1:
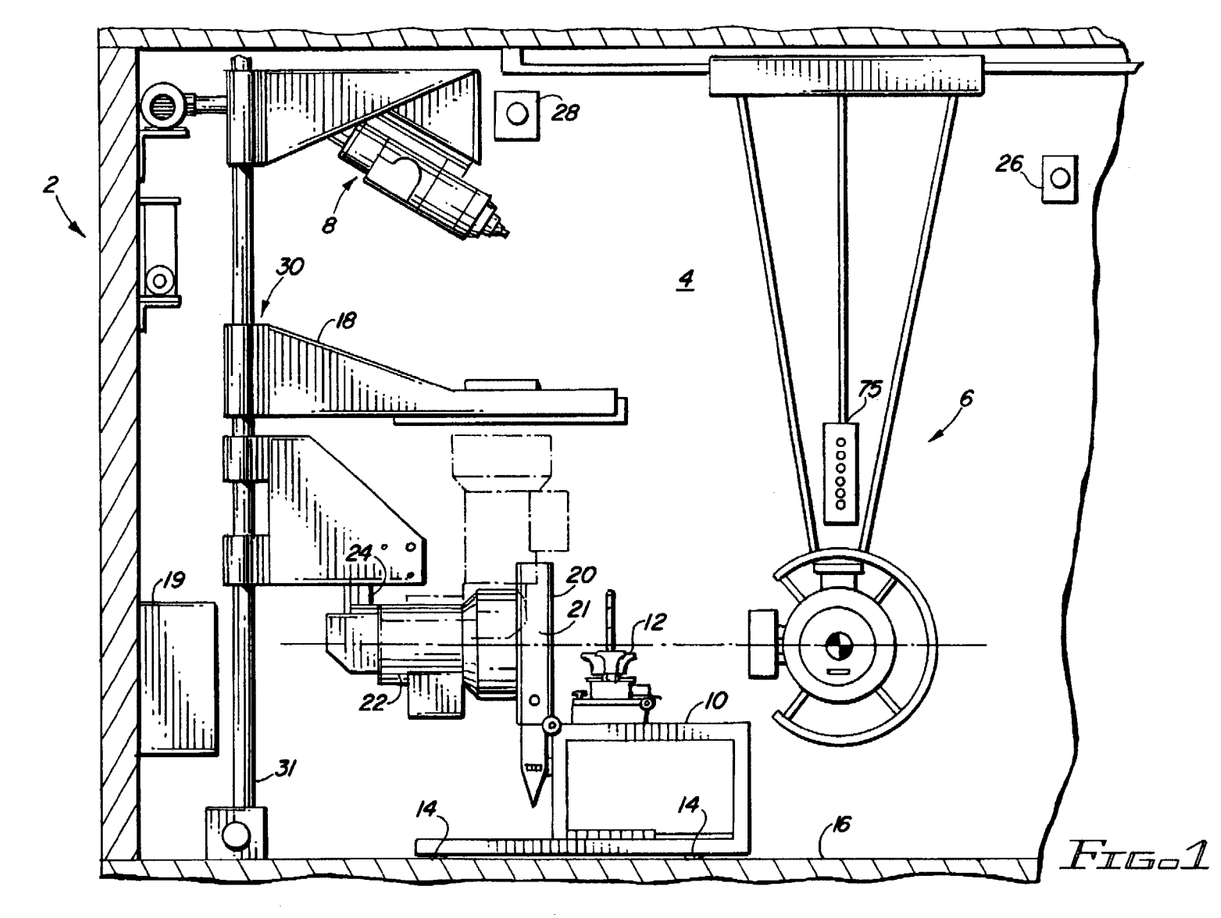
FIG. 1 is a diagrammatic representation of a lead room according to the invention and showing the system components therein.

A lead room 2 includes a large enclosure 4 which houses all electrical equipment, wiring harnesses, conduit junctions, etc. required by the system. The doors to enclosure 4 (not otherwise shown) have viewing windows as will be recognized as desireable. Enclosure 4 houses all system components which function as will next be described.

A conventional x-ray tube and housing assembly 6 includes a 320 kv, 5 ma (constant potential) device. The focal spot size is less than 1.0 mm and the housing assembly is arranged for motion control about three axes X, Y and Z, either remotely (control room 32, FIG. 2) or via an operator hand held pendant 75 (lead room 2). In addition, manual manipulation of 2 axes, i.e. rotate Z and rotate X, is possible. The purpose of conventional x-ray tube and housing assembly 6 is ideal to effectively inspect thicker cross sectional components and more dense materials. A small focal spot size and collimated x-ray beam provide very good to excellent analog images.

A microfocus x-ray tube and housing assembly 8 is a Fein Focus 160 kv 2 ma device (interchangeable anode). The focal spot size is less than 50 microns. The tube housing assembly is arranged for motion control of one axis (Z) via remote control room 32 (FIG. 2) or an operator (lead room 2).

A large parts inspection table 10 is designed to support the weight of large heavy parts, such as 12, weighing, for example, up to 100 pounds. Motion control of four axes X, Y, Z, rotate via remote (control room 32) or operator interface 19 (lead room 2) is possible. Additionally, manual manipulation of one axis tilt can be achieved.

The purpose of large part inspection table 10 is to properly position large parts being x-ray inspected in order to obtain optimum coverage and sensitivity. Table 10 has limit switches (not otherwise shown) for motion control and automatic reverse and casters, such as 14, moveable on floor guide rails 16 for variable positioning. All motion is computer programmed for accuracy and repeatability, said programming being well within the capability of those skilled in the art. Precision ball screws and DC driven stepper motors permit precise movement in small increments.

A small parts inspection tray 18 is designed for motion control about three axes (X, Y, Z) via remote (control room 32) or operator interface 19 (lead room 2). Motion is accomplished in a manner similar to that described for large parts table 10 and is likewise computer programmed for accuracy and repeatability.

The purpose of small parts inspection tray 18 is to properly position small light weight parts being x-ray tested for optimum coverage and sensitivity.

Figure 2:
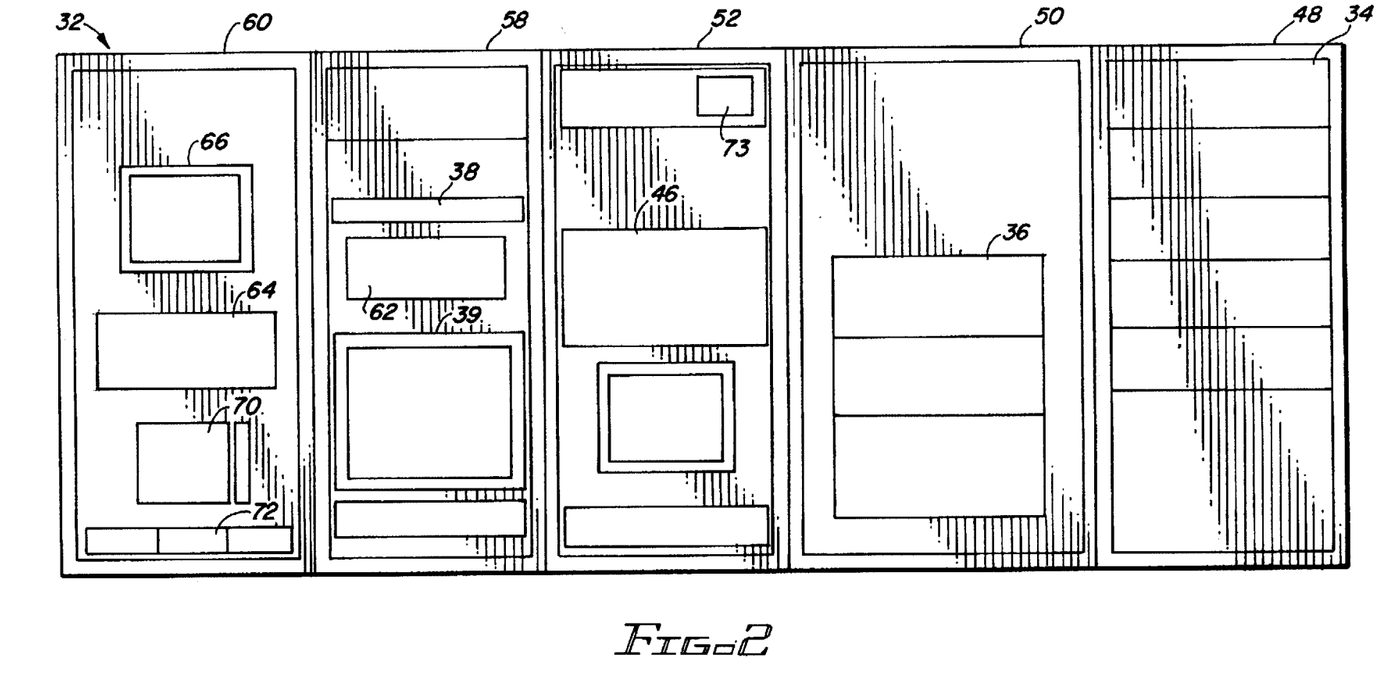
FIG. 2 is a diagrammatic representation of a control room according to the invention and showing the system components therein.

Lead shutters 20 include four independent panes of movement in shutter window 21. The shutters have a lead thickness of, for example, 0.7 inches per pane and are remotely controlled (control room 32). They are pivotable from zero to ninety degrees for dual ray inspection (conventional and microfocus). The purpose of shutters 20 is to reduce or eliminate radiation from striking an image intensifier 22 thus preventing a "flair up" on a display monitor 39 (FIG. 2). The lead shutters mask the radiation by offering a narrow yet highly usable window on image intensifier 22. The masking effect of radiation adds to the quality of the resulting analog image and the resulting digitized output.

Image intensifier 22 is housed in a housing assembly 23. Image intensifier 22 has a dual field capability to vary magnification of images. Housing assembly 23 is arranged to pivot from zero to ninety degrees for dual x-ray application (conventional and microfocus). When radiation from either source (conventional or microfocus) impinges on the image intensifier face, this energy source is focused as a signal onto the usable portion of image intensifier 22. The signal is highly amplified and presented at the focal plane of a CCD image acquisition camera 24 equipped with remote control lenses for zoom, iris and focus. It will be appreciated that image intensifier 22, arranged as aforementioned, replaces the use of x-ray film and permits the capture of high quality analog images which are ready for digital image enhancement and reconstruction, the same not being heretofore possible.

Image acquisition camera 24 is a high resolution video camera having a one-half inch image format (768 pixels horizontal by 493 pixels vertical resolution). The image acquisition camera is fitted with a remote control lens capable of manipulating zoom, iris and focus adjustment. It will be appreciated that image acquisition camera 24 will transfer analog live video images to a computer (control room 32), where the image is digitally processed. A remote control lens is used in conjunction with other equipment to amplify and enhance the analog video images.

Surveillance (video) cameras 26 and 28 (FIG. 1) are provided. Camera 28 is stationary and camera 26 is arranged with a remote control motorized arm for area pan and scroll. Camera 26 is also fitted with a lens capable of manipulating zoom and focus adjustment. The surveillance cameras provide live surveillance information to the operator of the x-ray system. This information is beneficial since it provides location data relative to a system component, i.e. the x-ray tube, and its proximity to the part being examined. The surveillance cameras also provide visual input useful during evaluation of the part being inspected. To this extent, information is revealed as to the location of a potential x-ray indication in a weldment and/or casting and its position to a feature on that part. All of the interaction between the cameras and operator is performed remotely in control room 32.

An x-ray system manipulator 30 supports Z axis movement of microfocus x-ray tube 8, small parts inspection tray 18 and image intensifier 22. Three ceiling to floor mounted ball screws such as 31 (FIG. 2) allow individual Z axis movement of the aforementioned three components. Additionally, the entire manipulator simultaneously moves all three components along the X axis for system repositioning. Motion control of all axes is achieved via remote control room 32 or operator interface 19 (lead room 2). The system is fitted with safety travel limit switches and wall mounted position gauges (not shown) for readout. It will be appreciated that system manipulator 30 provides precise movement of the system components which are rigidly affixed to the manipulator. The positioning of image intensifier 22, microfocus x-ray tube 8 and parts tray 18 is paramount in obtaining high quality x-ray analog and digital images. Position gauge readouts provide repeatability as is desireable. Microfocus x-ray manipulator 30 will be further described with reference to FIGS. 5–11.

With reference to FIG. 2, the components in control room 32 are shown and will next be described. These components include: a conventional x-ray controller 34, a microfocus x-ray controller 36; position readout gages 46; a video synthesizer 38; and a tape playback/surveillance monitor 70. The above components are disposed in racks 48, 50, 52, 58 and 60, respectively, and which racks are disposed in control room 32.

Conventional x-ray controller 34 produces up to 320 kv, 5 ma. With dual selectable focal spot sizes, the controller is programmable and imparts to the system the capability control to control kv, ma and time of x-ray exposure using preset parameters.

Microfocus x-ray controller 36 produces up to 160 kv, 2 ma and is semi-automatic with presets. It has adjustable beam alignment. The controller has the capability to control kv, ma and time of x-ray exposure using preset parameters and in these respects, is similar to x-ray controller 34.

Video synthesizer 38 includes a video out switch which selects between processed (enhanced) and unprocessed (normal) viewing modes. A video mode switch selects the polarity of input video signals either not affected or reversed. An edge mode switch selects positive, negative or plus edge modes. Video level control adjusts video gain and edge level control adjusts edge gain. An edge width selector switch provides adjustment from zero to three hundred ns in fifty ns steps. Video synthesizer 38 is used to enhance analog video signals without digital signal manipulation. The main functions are shifted between pixels and reverse video signals for a different perspective.

Video synthesizer 38 includes a display monitor 39 with 1280 pixels horizontal by 768 pixels vertical. The monitor is used to view output from computer 73 in either a normal or enhanced mode. The output from this monitor is passed through a video printer 62 for screen prints and through a video cassette recorder 64 to record inspection of parts. A playback monitor 66 is used in connection with video cassette recorder 64 in order to view what was recorded on the cassette. This allows operators to review inspection tapes while the display monitor is in use for production runs.

Surveillance monitor 70 and control 72 include a low profile video monitor (525 lines of resolution) 70. Pan, tilt, zoom and iris controls are provided. This equipment is used in conjunction with control surveillance cameras 26 and 28 in lead room 2, as heretofore noted. A manipulator control panel 46 allows operators to manually perform motion control functions for the various equipment in lead room 2. This is a paramount feature for operators during initial set-up of the part being examined prior to automated inspection. One set of controls operates both cameras simultaneously.

Manipulator control panel interface 19 (FIG. 1) is a series of direct wire toggle switches for manually controlling from lead room 2 motion of both x-ray tubes, image intensifier and inspection tray.

Figure 3:
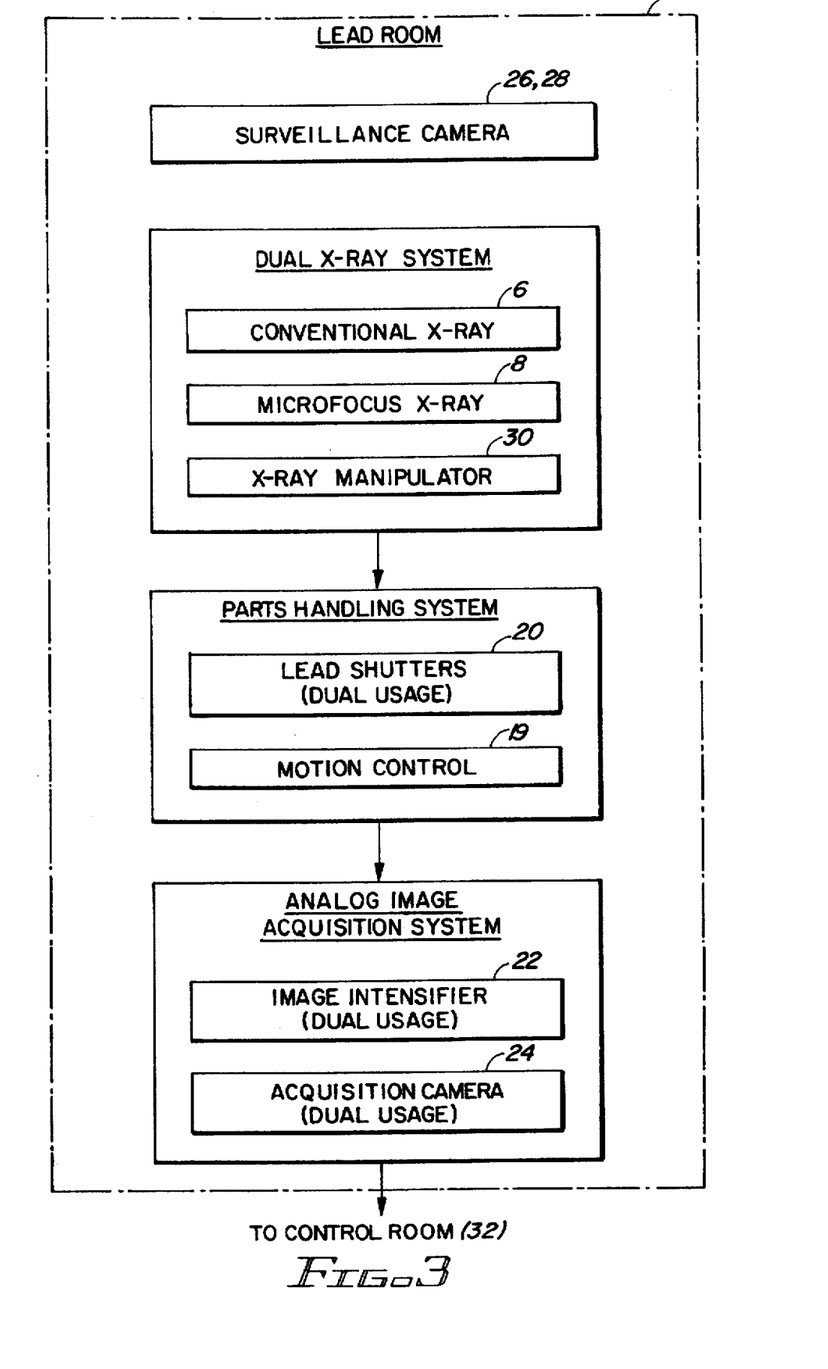
FIG. 3 is a flow chart illustrating the functions performed in the lead room.
Figure 4:
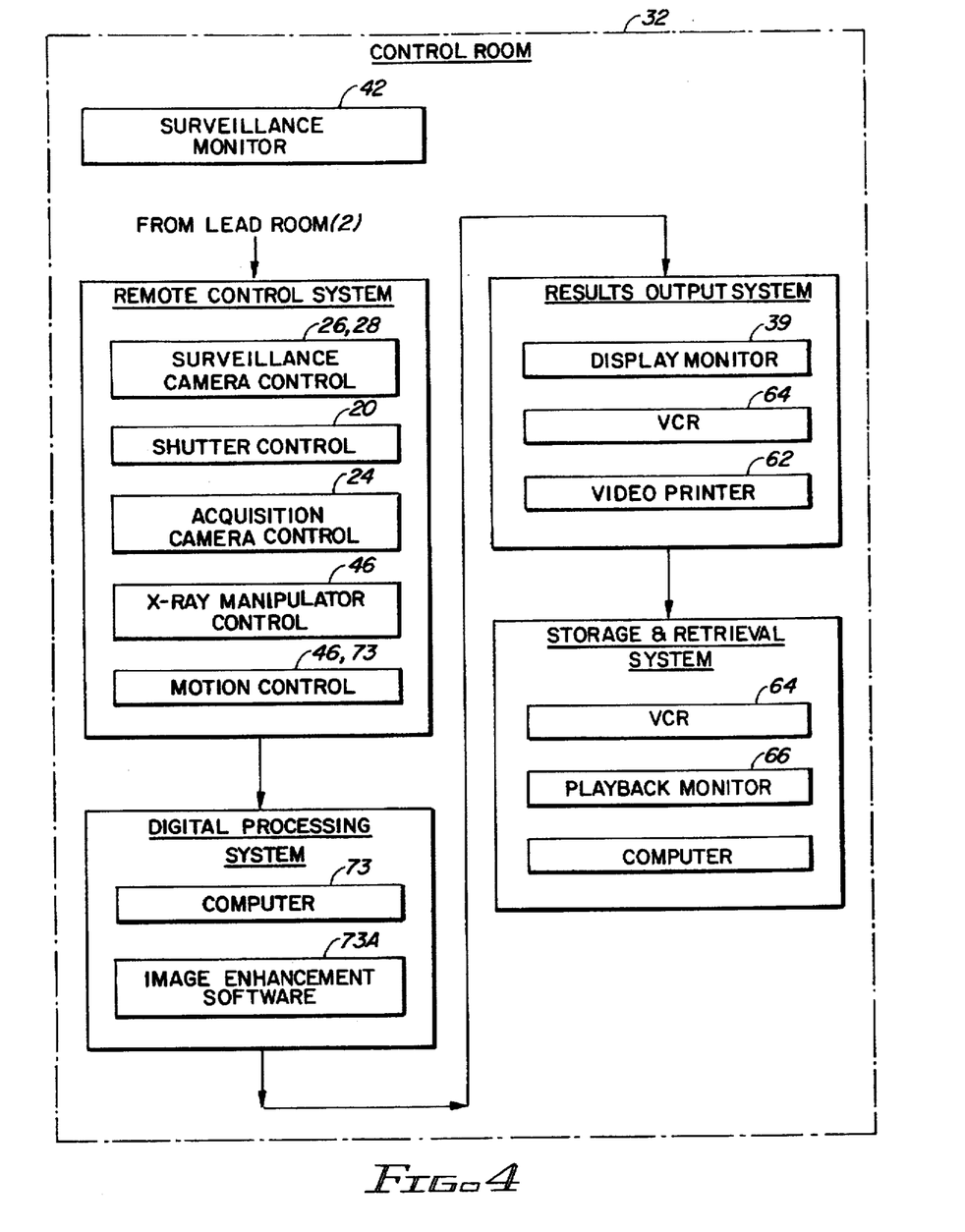
FIG. 4 is a flow chart illustrating the functions performed in the control room.

Computer 73 is a 386/25 personal computer with 120 mb hard drive, 4 mb memory, 1.2 mb floppy, DOS 3.1 and appropriate image enhancement software 52A. The computer includes a touch screen for input and a joy stick for certain software applications. The software allows the use of user defined modules that perform control for equipment in the lead room. All automated inspection, motion control and digital image enhancement is accomplished through computer 73. The computer receives a live analog video signal from the appropriate image acquisition camera and transforms it into a digital binary image. In this state, the digitized image is further developed using an array of image enhancement routines to produce a resultant composite image that portrays high quality resolution and definition. Mathematical imaging routines allow for low contrasting images to be recontoured using real time averaging. Storage and/or retrieval is accomplished on the computer with optional output to peripherals such as hard driver, video printers or video cassette recorders. The flow charts of FIGS. 3 and 4 illustrate the general systems and functions performed in lead room 2 and control room 32, with the equipment indicated in the Figures.

Thus, lead room 2 includes the earlier described dual x-ray system (6, 8, 30); the parts handling system (19, 20); and the analog image acquisition system (22, 24), and is interfaced with control room 32.

Control room 32, interfaced with lead room 2, includes a remote control system (20, 24, 28, 46, 73); a digital processing system (73, 73A, 39, 64, 62) and a storage and retrieval system (64, 66, 73). Each of the noted systems includes components earlier described.

Microfocus x-ray manipulator 30 (FIG. 1) is used to accurately position and radiographically test smaller, light weight parts using microfocus x-ray source 8 (FIG. 1). To this extent, as particularly shown in FIGS. 5–11, manipulator 30 includes a bracket 100 which supports a microfocus x-ray source 102; a bracket 104 which supports an inspection tray 106; and a bracket 108 which supports an image intensifier 110.

Figure 5:
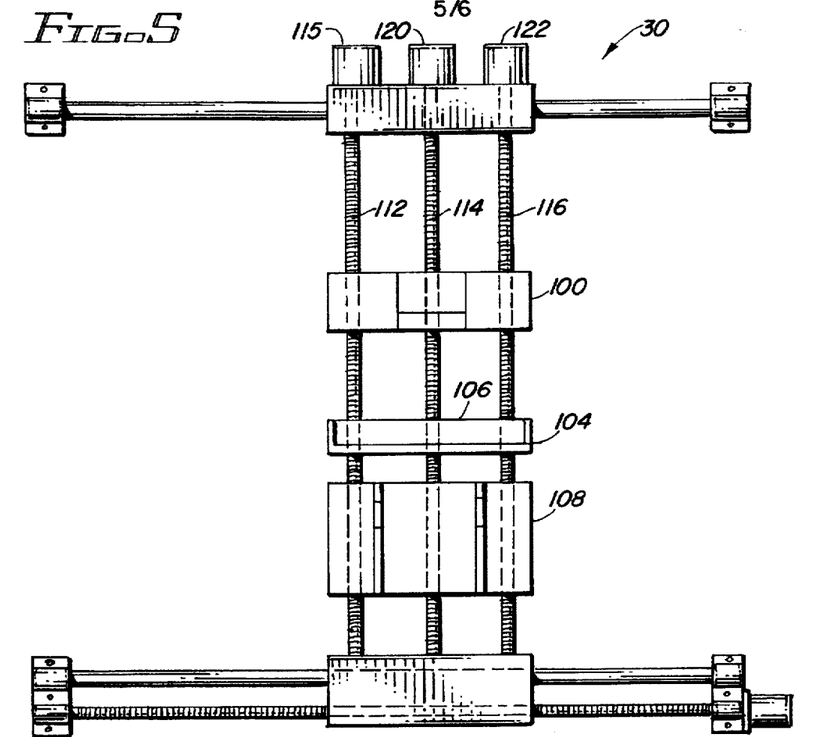
FIG. 5 is a diagrammatic front view of a microfocus x-ray manipulator according to the invention.
Figure 6:
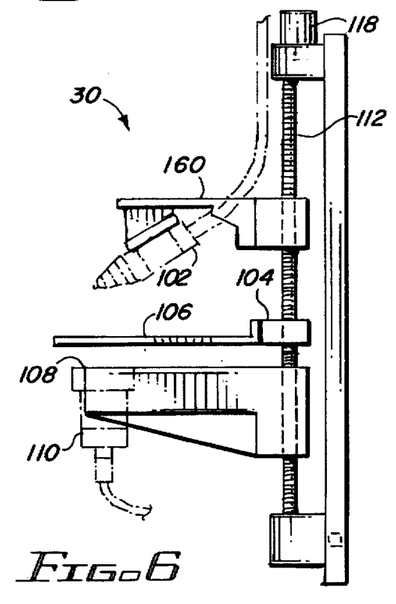
FIG. 6 is a diagrammatic side view of a microfocus x-ray manipulator.

Brackets 100, 104 and 108 are motion controlled for single axis movement via ball screws 112, 144 and 116 coupled to DC motors 118, 120 and 122, respectively.

Figure 8:
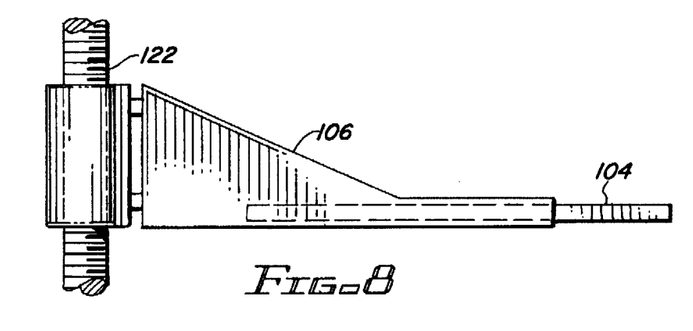
FIG. 8 is a diagrammatic side view of a tray bracket according to the invention.
Figure 9:
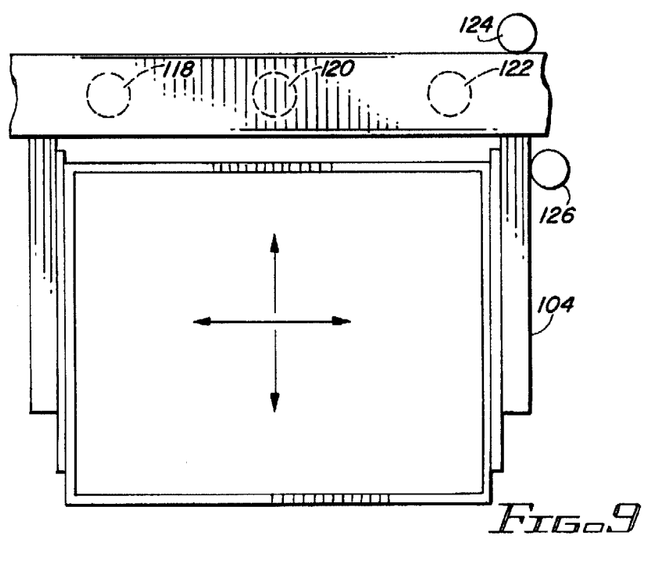
FIG. 9 is a diagrammatic top view of the tray bracket.

With reference to FIGS. 8 and 9, sample tray 106 is motion controlled for two axes of movement indicated by the arrows in FIG. 9 using stepper motors 124 and 126 to allow accurate positioning of the parts being x-rayed.

Figure 7:
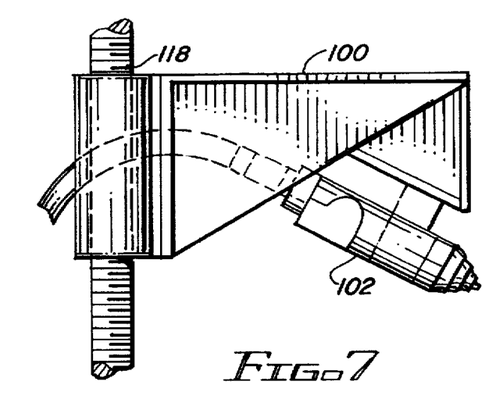
FIG. 7 is a partial diagrammatic side view of the microfocus manipulator.

With reference to FIG. 7, bracket 108 is controlled via the appropriate ball screw and DC motor to permit proper position and magnification of microfocus x-ray source 102 as will now be understood.

Figure 10:
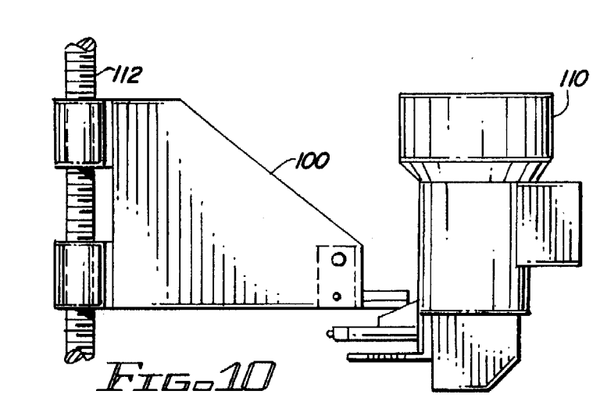
FIG. 10 is a diagrammatic side view of an intensifier bracket according to the invention, with the intensifier positioned at 0 degrees.
Figure 11:
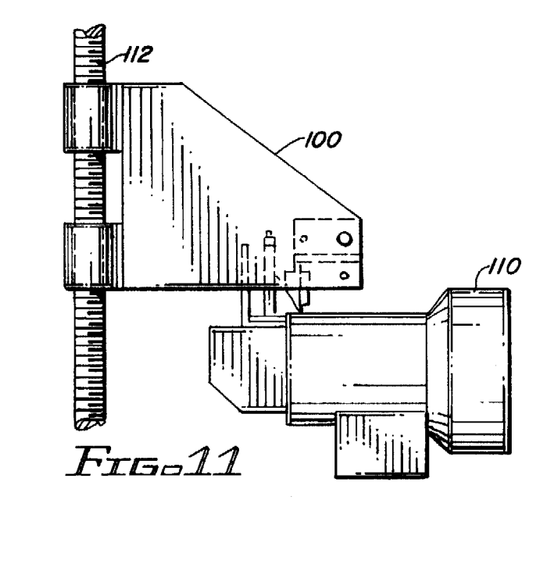
FIG. 11 is a diagrammatic side view of the intensifier bracket with the intensifier positioned at 90 degrees.

With reference to FIGS. 10 and 11, it will be appreciated that x-ray image intensifier 110 converts x-ray light into visible light. Bracket 100 is controlled via ball screw 112 and the appropriate DC motor to allow proper positioning of intensifier 110 with respect to the x-ray source and inspection sample tray. Visible light can then be fed into a video camera (not otherwise shown). Bracket 100 supports intensifier 110 in two angles: 0 degrees and 90 degrees as shown in FIGS. 10 and 11, respectively.

With the above description of the invention in mind, reference is made to the claims appended hereto for a definition of the scope of the invention.

What is claimed is:

1. A manipulator for a microfocus x-ray source in a digital real-time x-ray system, being enclosed along with a conventional x-ray source in a lead room separated from a control room, comprising:

a first bracket which supports the microfocus x-ray source, a second bracket which supports an inspection tray and a third bracket which supports an image intensifier;

means for controlling the first, second and third brackets for single axis movement; and means for controlling the inspection tray for two axes movement to allow for accurate positioning of parts being x-rayed.

2. A manipulator as described by claim 1, wherein:

the first, second and third brackets are controlled for single axis movement via respective ball screws coupled to DC motors.

3. A manipulator as described by claim 1, wherein:

the means for controlling the inspection tray for two axis of movement includes a stepper motor for each of the two axes.

4. A manipulator as described by claim 1, wherein:

the first bracket is controlled to permit proper positioning and magnification of the microfocus x-ray source.

5. A manipulator as described by claim 1, wherein:

the third bracket is controlled to permit proper positioning of the image intensifier with respect to the x-ray source and inspection tray.

6. A manipulator as described by claim 1, wherein:

the third bracket supports the intensifier at 0 degrees and at 90 degrees.

7. A manipulator for a microfocus x-ray source, comprising:

a first bracket which supports the microfocus x-ray source;

a second bracket which supports an inspection tray;

a third bracket which supports an image intensifier;

the first, second and third brackets controlled for single axis movement via respective ball screws coupled to DC motors;

a pair of stepper motors for controlling the inspection tray for two axis movement to allow for accurately positioning of parts being x-rayed;

the first bracket controlled to permit proper positioning of the image intensifier with respect to the x-ray source and inspection tray; and the third bracket supporting the intensifier at 0 degrees and at 90 degrees.

8. A manipulator as described by claim 7, further including a manipulator control panel which is operator-operated for controlling the first, second and third brackets for single axis movement, and for controlling the inspection tray for two axes movement.

9. A manipulator as described by claim 8, wherein:

said manipulator control panel is also operator-operated for controlling the position of the microfocus x-ray source.

* * * * *